US012196374B2

(12) United States Patent
Edoardo et al.

(10) Patent No.: US 12,196,374 B2
(45) Date of Patent: Jan. 14, 2025

(54) APPARATUS AND SYSTEM FOR GAS COMPRESSION AND THE METHOD FOR COMPRESSION OF A GAS

(71) Applicant: GAS TECHNOLOGIES L.L.C., Walloon Lake, MI (US)

(72) Inventors: Ongaro Edoardo, Martellago (IT); Walter Breidenstein, Boyne Falls, MI (US)

(73) Assignee: Gas Technologies L.L.C., Walloon Lake, MI (US)

( * ) Notice: Subject to any disclaimer, the term of this patent is extended or adjusted under 35 U.S.C. 154(b) by 639 days.

(21) Appl. No.: 17/415,097

(22) PCT Filed: Dec. 17, 2019

(86) PCT No.: PCT/US2019/066764
§ 371 (c)(1),
(2) Date: Jun. 17, 2021

(87) PCT Pub. No.: WO2020/131821
PCT Pub. Date: Jun. 25, 2020

(65) Prior Publication Data
US 2022/0065401 A1  Mar. 3, 2022

Related U.S. Application Data

(60) Provisional application No. 62/780,636, filed on Dec. 17, 2018.

(51) Int. Cl.
*F17C 5/06* (2006.01)
*B01J 19/24* (2006.01)
(Continued)

(52) U.S. Cl.
CPC ............... *F17C 5/06* (2013.01); *B01J 19/24* (2013.01); *F04B 41/02* (2013.01); *F17C 13/025* (2013.01);
(Continued)

(58) Field of Classification Search
CPC .......... F17C 5/06; F17C 13/025; F17C 13/02; F17C 2205/0335; F17C 2227/0135;
(Continued)

(56) References Cited

U.S. PATENT DOCUMENTS 4,515,516 A * 5/1985 Perrine ................ F17C 5/06
222/61
4,902,207 A   2/1990 Hembree et al.
(Continued)

FOREIGN PATENT DOCUMENTS

IT   UD 20090011 A1   7/2010
KR   101668672 B1    10/2016

OTHER PUBLICATIONS

International Search Report & Written Opinion mailed Apr. 14, 2020 for PCT/US2019/066764 filed Dec. 17, 2019, 15 pgs.
(Continued)

*Primary Examiner* — Lessanework Seifu
(74) *Attorney, Agent, or Firm* — Brooks Kushman P.C.

(57) ABSTRACT

An apparatus and method of compressing a gas is provided. The system includes a gas storage tank and a liquid holding tank and a hollow cylinder. A piston is disposed in the hollow cylinder dividing the hollow cylinder into a first compartment and a second compartment. A gas collector tank is in fluid connection with the first compartment by an outline line. A radiator is provided in fluid connection with the second compartment and the liquid holding tank. The
(Continued)

system also contains a pump. The apparatus system may also be coupled to a reactor system oxidizes a hydrocarbon-containing gas.

21 Claims, 6 Drawing Sheets (51) Int. Cl.
*F04B 41/02* (2006.01)
*F17C 13/02* (2006.01)

(52) U.S. Cl.
CPC .... *F17C 13/026* (2013.01); *F17C 2205/0335* (2013.01); *F17C 2227/0135* (2013.01); *F17C 2250/043* (2013.01); *F17C 2250/0439* (2013.01); *F17C 2270/05* (2013.01)

(58) Field of Classification Search
CPC ........ F17C 2250/043; F17C 2250/0439; F17C 2270/05; F04B 41/02; B01J 19/24
See application file for complete search history.

(56) References Cited

U.S. PATENT DOCUMENTS

| | | | |
|---|---|---|---|
| 4,968,329 | A | 11/1990 | Keefer |
| 7,910,787 | B2 | 3/2011 | Pawlak et al. |
| 10,099,199 | B2 | 10/2018 | Rao et al. |
| 2006/0223892 | A1* | 10/2006 | Pawlak .............. B01D 53/1487 518/702 |
| 2009/0229701 | A1* | 9/2009 | Allidieres ................ F17C 7/00 141/2 |
| 2012/0047884 | A1 | 3/2012 | McBride et al. |
| 2015/0240799 | A1 | 8/2015 | Obrejanu et al. |
| 2015/0354754 | A1 | 12/2015 | Whiteman et al. |

OTHER PUBLICATIONS

Extended European Search Report dtd Jul. 18, 2022 for EP Appn. No. 19901034.9, 8 pgs.

* cited by examiner

Fig. 6

APPARATUS AND SYSTEM FOR GAS COMPRESSION AND THE METHOD FOR COMPRESSION OF A GAS

CROSS-REFERENCE TO RELATED APPLICATIONS

This application is the U.S. national phase of PCT Appln. No. PCT/US2019/066764 filed Dec. 17, 2019, which claims the benefit of U.S. provisional application Ser. No. 62/780,636 filed Dec. 17, 2018, the disclosures of which are hereby incorporated in their entireties by reference herein.

TECHNICAL HELD

In at least one aspect, the present invention is related to a gas compression system.

BACKGROUND

It is well known that gas and gas mixtures can be compressed in order to increase pressure and stored. Fluid controls many compression systems. Typically, synthetic oils are pumped into only one cylinder's side that result in movement of a piston and compress the gas. The high temperature and pressure required to result in movement of the piston require use of synthetic oil. Typically, the gas must be provided in isolation systems of pistons to avoid the mixture of oil and gas.

As we know, we can compress gas, or gas mixture, in order to increase the pressure, for example, between 10 and 600 bars, and put them inside vessels tanks and others, the application of one or more plants to determine the gas compression.

The compression plants are typical used for the alternative technic, one or more mono stage cylinders or one or more double-stage cylinders that included pistons compression.

This kind of compression plant is controlled by liquid fluid of control. Generally we refer to synthetic oils that are pumped into only one cylinder's side, that determinate the piston's movement about the alternation of compression and suction. The high temperature and pressure regarding the piston's movement needs the application of synthetic oil, in order to maintain during the proceed the operational characteristics unaltered.

The gas must be unaltered especially in those kinds of applications as the refilling of oxygen, hydrogen, methane, helium and the like into vessels or cylinders. For this reason it is necessary to provide an isolation system of pistons to avoid the mixture of synthetic oil and gas.

In order to maintain the plant's costs lower, usually is normal to use oil, even if this determine the mixture of the oil with gas, due to the strong components usury. This happened especially in several fields of gas compression, for example the utilization of oxygen, where is not allowed the presence of lubricating oils, that are dangerous in case of fire and or explosions.

Another inconvenient is about the high temperature that are created by the compression phase. This high temperature causes the degree increment about the compressed gas, that can create the thermodynamic variation of gas expansion, with several variations of compress conditions inside the vessel.

Obviously to reach the cooled gas with the correct pressure, is necessary to compress it in higher pressure and wait the balancing of this temperature inside the tank. In this situation, the vessel, in high temperature is not immediately manage manually.

Accordingly, there is a need for improvement of a low-cost gas compression system that avoids thermodynamic variation of expansion without contamination.

SUMMARY

In at least one aspect, the present invention relates generally to a novel system for the process of compressing and cooling gasses.

In another aspect, a gas compression system is provided. The system includes a gas storage tank and a liquid holding tank. In a refinement, the gas storage tank contains an uncompressed gas. A hollow cylinder is in fluid connection with both the gas storage tank and the liquid holding tank. A piston is disposed within the hollow cylinder. The piston divides the hollow cylinder into two compartments. A gas collector tank is in fluid connection with one compartment. A radiator is also provided and is in fluid connection with the second compartment of the hollow cylinder and the liquid holding tank. The system also includes a pump in fluid connection with the liquid holding tank and the second compartment of the hollow cylinder.

In another aspect, a gas compression system is provided. The system includes a first cylinder and a second cylinder connected by a sealing gasket. The system also includes two pistons. The first piston is slidably positioned in the first cylinder and defines a first compartment between the first piston and the sealing gasket. The second piston is slidably positioned in the second cylinder and defines a second compartment between the second piston and the sealing gasket. A stem connects the first piston and the second piston. A gas storage tank is in fluid connection with the first cylinder and first compartment. A liquid holding tank is in fluid connection with the second compartment and second cylinder. A pump is provided in fluid connection with the liquid holding tank. A gas collector tank is in fluid connection with the second compartment and first cylinder by an outlet line. A radiator is also included in fluid connection with the second cylinder, second compartment, and liquid holding tank.

In another aspect, a reaction assembly is provided. The reactor system includes a reactor system that oxidizes a hydrocarbon-containing gas. The assembly also includes a gas storage tank and a liquid holding tank. A hollow cylinder is in fluid connection with both the gas storage tank and the liquid holding tank. A piston is disposed within the hollow cylinder. The piston divides the hollow cylinder into two compartments. A gas collector tank is in fluid connection with one compartment. A radiator is also provided and is in fluid connection with the second compartment of the hollow cylinder and the liquid holding tank. The assembly also includes a pump in fluid connection with the liquid holding tank and second compartment of the hollow cylinder.

In another aspect, a gas compress plant can be constructed at a low budget by including simple components that compress gas with reduced contamination while avoiding the thermodynamic variation of gas during the compression phase.

In another aspect, the present invention provides the compression and cooling of simple and dangerous gases. In every single phase of this procedure, the gas must be separated from external agents as active agents, oils, dust and other organs that can change the chemical composition of gas.

In another aspect, the compression systems set forth herein provide the application for the refueling of technical pure gas, ultrapure, and inflammable as oxygen, hydrogen and all gas mixtures where there is a need for the chemical composition to be maintained unaltered.

In another aspect, a control circuit for the control fluid includes one or more coolers (e.g., fans with optional radiators) that pass the control fluid into compression organs (e.g. compression cylinders). The coolers can reduce the control fluid temperature.

In another aspect, a control fluid used to move a piston to compress a gas is water. Water is simpler and more economic than synthetic oils. Moreover, a single contact with a fluid control as water avoid risks of contaminations normally caused by oils.

Advantageously, the compression system set forth herein all refilling of vessels or tanks for high-pressure compression gas.

DETAILED DESCRIPTION

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the term "polymer" includes "oligomer," "copolymer," "terpolymer," and the like; molecular weights provided for any polymers refers to weight average molecular weight unless otherwise indicated; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

The term "substantially," "generally," or "about" may be used herein to describe disclosed or claimed embodiments. The term "substantially" may modify a value or relative characteristic disclosed or claimed in the present disclosure. In such instances, "substantially" may signify that the value or relative characteristic it modifies is within±0%, 0.1%, 0.5%, 1%, 2%, 3%, 4%, 5% or 10% of the value or relative characteristic.

The term "gas" as used herein mean a single gaseous component or a mixture of gaseous components.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1 to 2.1 the following numbers 1.2, 1.3, 1.4, 1.5, 1.6, 1.7, 1.8, 1.9, and 2.0 can be selected as lower or upper limits. In the specific examples set forth herein, concentrations, temperature, and reaction conditions (e.g. pressure, pH, etc.) can be practiced with plus or minus 50 percent of the values indicated rounded to three significant figures. In a refinement, concentrations, temperature, and reaction conditions (e.g., pressure, pH, etc.) can be practiced with plus or minus 30 percent of the values indicated rounded to three significant figures of the value provided in the examples. In another refinement, concentrations, temperature, and reaction conditions (e.g., pH, etc.) can be practiced with plus or minus 10 percent of the values indicated rounded to three significant figures of the value provided in the examples.

In the examples set forth herein, concentrations, temperature, and reaction conditions (e.g., pressure, pH, flow rates, etc.) can be practiced with plus or minus 50 percent of the values indicated rounded to or truncated to two significant figures of the value provided in the examples. In a refinement, concentrations, temperature, and reaction conditions (e.g., pressure, pH, flow rates, etc.) can be practiced with plus or minus 30 percent of the values indicated rounded to or truncated to two significant figures of the value provided in the examples. In another refinement, concentrations, temperature, and reaction conditions (e.g., pressure, pH, flow rates, etc.) can be practiced with plus or minus 10 percent of the values indicated rounded to or truncated to two significant figures of the value provided in the examples.

Throughout this application, where publications are referenced, the disclosures of these publications in their entireties are hereby incorporated by reference into this application to more fully describe the state of the art to which this invention pertains.

In at least one embodiment, a gas compression system is provided. The system includes a gas storage tank and a liquid holding tank. A hollow cylinder is in fluid connection with both the gas storage tank and the liquid holding tank. A piston is disposed within the hollow cylinder. The piston divides the hollow cylinder into a first compartment and second compartment. A gas collector tank is in fluid connection with first compartment by an outlet line. A radiator is also provided and is in fluid connection with the second compartment of the hollow cylinder and the liquid holding tank. The system also includes a pump in fluid connection with the liquid holding tank and second compartment of the hollow cylinder.

In a refinement, the system includes a temperature sensor operatively associated with the outlet line to measure the temperature of compressed gas. In another refinement the system includes a pressure sensor operatively associated with the outlet line to measure the pressure of compressed gas. The system may also have check valves disposed between the gas storage tank and first compartment and a second check valve disposed between the first compartment and the gas collector tank. The system may also have a first exchange valve disposed between the second compartment and the pump and a second exchange valve disposed between the second compartment and the radiator. In refinement the system may also have a limit switch associated with hollow cylinder. In further refinement the piston contains a magnet.

In another refinement, the system comprises a second hollow cylinder in fluid connection with the gas storage tank and liquid holding tank, a second piston slidably positioned in the second hollow cylinder dividing it into a third compartment and a fourth compartment. In this refinement, the third compartment is in fluid connection with the gas storage tank and the gas collector tank while the fourth compartment is in fluid connection with the pump and the radiator.

In at least another embodiment, a gas compression system is provided with two overlapping cylinders. The system comprises a first cylinder and second cylinder connected by a sealing gasket. The system also includes two pistons. The first piston is slidably positioned in the first cylinder and defines a first compartment between the first piston and the sealing gasket. The second piston is slidably positioned in the second cylinder and defines a second compartment between the second piston and the sealing gasket. A stem connects the first piston and the second piston. A gas storage tank is in fluid connection with the first cylinder and first compartment. A liquid holding tank is in fluid connection with the second compartment and second cylinder. A pump is provided in fluid connection with the liquid holding tank. A gas collector tank is in fluid connection with the second compartment and first cylinder by an outlet line. A radiator is also included in fluid connection with the second cylinder, second compartment, and liquid holding tank.

In a refinement, the system includes a temperature sensor operatively associated with the outlet line to measure the temperature of compressed gas. In another refinement the system includes a pressure sensor operatively associated with the outlet line to measure the pressure of compressed gas. The system may also have a first check valve disposed between the first compartment and the gas storage tank and a second check valve disposed between the first compartment and the gas collector tank. The system may also have a first exchange valve disposed between the second compartment and the pump and a second check valve disposed between the second compartment and the radiator. In refinement the system may also have two limit switches associated with the second cylinder laterally spaced from one another. In further refinement, the second piston contains a magnet.

In at least another embodiment, a reaction assembly is provided. The reactor system includes a reactor system that oxidizes a hydrocarbon-containing gas. The assembly also includes a gas storage tank and a liquid holding tank. A hollow cylinder is in fluid connection with both the gas storage tank and the liquid holding tank. A piston is disposed within the hollow cylinder. The piston divides the hollow cylinder into two compartments. A gas collector tank is in fluid connection with one compartment. A radiator is also provided and is in fluid connection with the second compartment of the hollow cylinder and the liquid holding tank. The assembly also includes a pump in fluid connection with the liquid holding tank and second compartment of the hollow cylinder. In refinement, the system includes a temperature sensor operatively associated with the outlet line to measure the temperature of compressed gas.

In another refinement, the system includes a pressure sensor operatively associated with the outlet line to measure the pressure of compressed gas. The system may also have check valves disposed between the gas storage tank and first compartment and a second check valve disposed between the first compartment and the gas collector tank. The system may also have a first exchange valve disposed between the second compartment and the pump and a second exchange valve disposed between the second compartment and the radiator. In refinement the system may also have a limit switch associated with hollow cylinder. In further refinement the piston contains a magnet.

In another refinement, the system comprises a second hollow cylinder in fluid connection with the gas storage tank and liquid holding tank, a second piston slidably positioned in the second hollow cylinder dividing it into a third compartment and a fourth compartment. In this refinement, the third compartment is in fluid connection with the gas storage tank and the gas collector tank while the fourth compartment is in fluid connection with the pump and the radiator.

With reference to the attached figures, an installation according to the present invention is used for the compression of a gas, in this case, an oxygenate (e.g., methanol, formaldehyde, oxygen, alcohols, and the like) or other gases for fil ling cylinders for all types of use. As said, it is not excluded that the plant can be equally applied for the compression of other gases, or gas mixtures, such as methane or others. It should be appreciated that components of any subsystem described in a figure can be integrated into the systems of the other figure.

Figure 1:
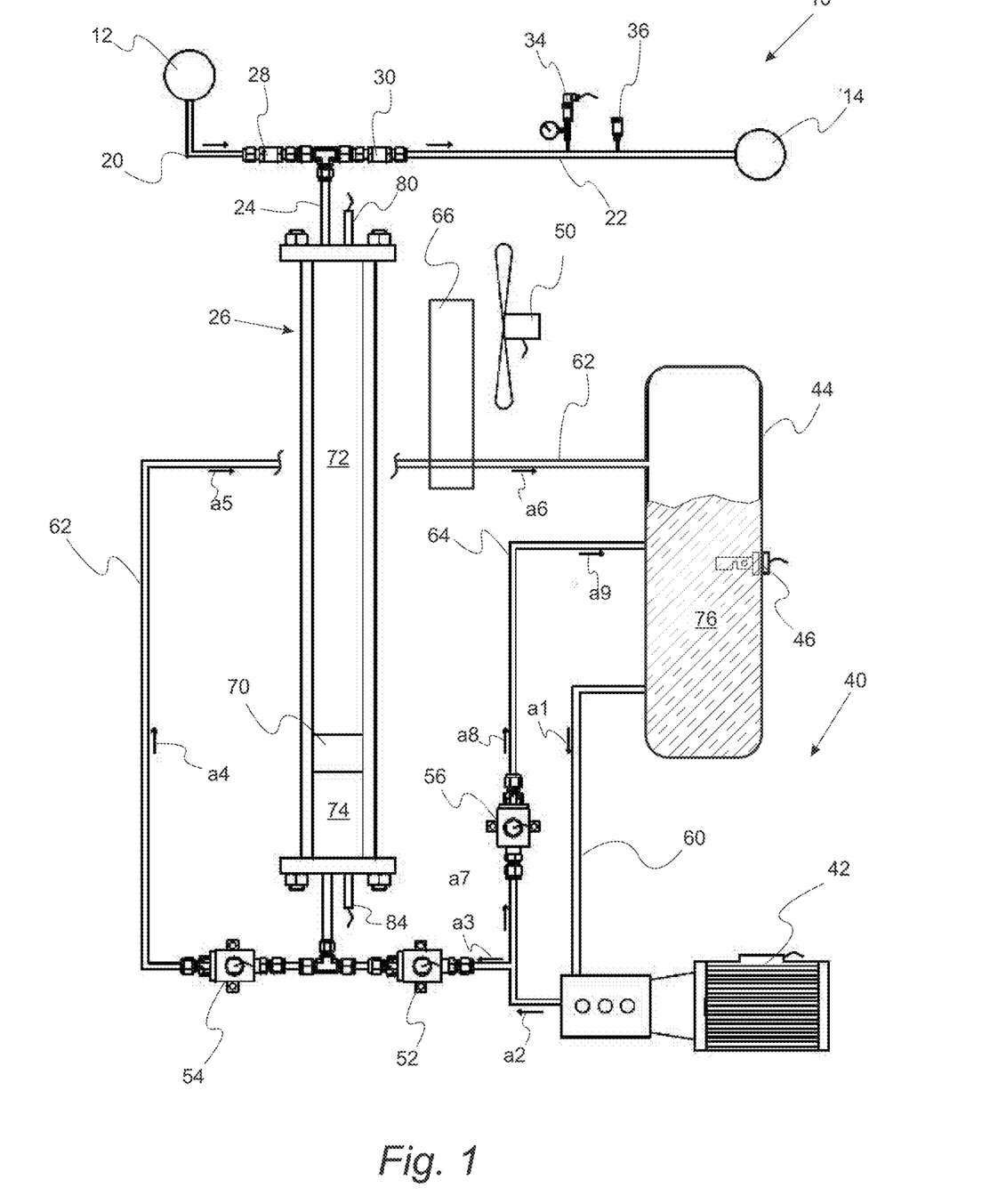
FIG. 1 provides a schematic of the gas compression system having a single compression cylinder

With reference to FIG. 1, gas compression system 10 includes gas inlet tank 12 and gas outlet tank 14. In a refinement, gas inlet tank 12 and gas outlet tank 14 is connected to one side of cylinder 26. Gas is introduced into cylinder 26 from gas inlet tank 12. Gas outlet tank 14 is of an adequate size to accumulate a predetermined minimum volume of compressed gas. Gas compression system 10 also includes a first inlet line 20 through which gas to be compressed flow from the inlet tank 12 and a second outlet line 22 which injects the compressed gas into gas outlet tank 14. The first line 20 is connected at column inlet line 24 to at least one compression cylinder 26 through check valves 28 and 30.

Moreover, downstream of the check valves into the outlet direction of the gas, a pressure transducer 34 is operatively associated, arranged to detect the pressure at which the compressed gas is located inside the outlet line 22. Outlet line 22 includes a safety valve 36 to guarantee the gas pressures under control.

The control subassembly 40 includes an electric pump 42, or any fluid pumping device, a liquid holding tank 44 which optionally includes a level sensor 46. In a refinement, control subassembly 40 is a fluid (e.g., water) compression circuit. Control subassembly 40 also includes a heat exchanger 50 (e.g., a cooling fan) and a plurality of controllable valve (e.g., high-pressure valves 52, 54, 56) suitable for distributing the control fluid alternately in compression cylinder 26. The heat exchanger 50 is located at a position proximate to column 26 such that the control fluid (e.g., water) is maintained (e.g., cooled) to be at a predetermined controlled operating temperature. As set forth below, these components allow control fluid pumped by the electric pump 42 is alternatively pumped into cylinder 26 and liquid holding tanking 44 via coordinated operation of check valves 28 and 30 which are adapted to permit alternatively the gas inlet and of the compression cylinder 26 due to the orientation of their directionality.

In a refinement, a fluid temperature sensor is present in one or more of control fluid lines 60, 62, and/or 64 to keep the control fluid temperature under control. Control fluid line 60 connects liquid holding tank 44 to pump 42. In a further refinement, control fluid line 62 connect radiator 66 to liquid holding tanking tank 44. In another refinement, the control fluid flows through or proximate to radiator 66.

Piston 70 contacts perimetrically the inner circular surface of the cylinder 26 through the respective guide and gaskets selings, so as to make the two compartments substantially sealed between them, to divide hermetically the control fluid (water) and the fluid to be compressed (gas or gas mixture). In a refinement, piston 70 is slidably arranged to define two separate column spaces 72, 74 with variable volumes. The gas is introduced into and compressed in column space 72. The control fluid 76 in introduced into column space 74 in order to compress the gas.

The procedure for compressing a gas with gas compression system 10 follows. With reference to FIG. 1, the gas is introduced through the inlet line 20 of the compression circuit inside the cylinder 26. In particular, the gas is introduced into the cylinder 26 at a pressure of about 4 bar or 200 bar. At the same time, the electric pump 42 pumps the control fluid (e.g., water) inside the high-pressure fluid circuit, and the valve 52 open, directs the pumped control fluid towards the cylinder 26. The control fluid can be any liquids that do not compromise the chemical composition of gas being compressed. In a refinement, the control fluid is water. The electric pump 42 works with greater pressure on the control fluid and is sufficient to overcome the force caused by the gas during the compression phase. This condition causes the compression by the piston 70 to be raised by compressing the gas present inside it. This compression causes an exit of the gas from the cylinder 26 through the check valve 30, with consequent of the gas compression circuit, and compressed is introduced into the gas outlet tank 14. Arrows a1-a9 show the directions that the control fluid flows.

When the piston 70 reaches of the limit switch, the magnetic sensor 80 detects the magnet present inside the piston 70, the magnet is isolated and is not in contact with any of the fluids present in the cylinders. This condition detected by the sensor 80 causes the activation (i.e., opening) of valves 54 and 56 and at the same time the closing of the valve 52. Therefore, control fluid is directed to liquid holding tanking 44 by the force of the gas which pushes the piston 70 downwards. When the piston 70 is detected by the magnetic sensor 84, valves 54 and 56 close followed by the opening of valve 52. This allows the control fluid to flow into column 26 again thereby compressing the gas.

The alternate control fluid pumping and gas compression exchange is repeated until the pressure sensor 34 of the gas compression subassembly signals that the desired gas compression pressure has been reached inside gas outlet tank 14.

In another variation, compression system 10 includes one or a plurality of compression cylinders 26 alternately coordinated with each other to compress the gases. Characteristically, each of a a plurality of compression cylinders 26 are of the design set forth above. In particular, each cylinder is connected to a gas inlet line, gas outlet line, column inlet line and a control subassembly as set forth above.

Figure 2:
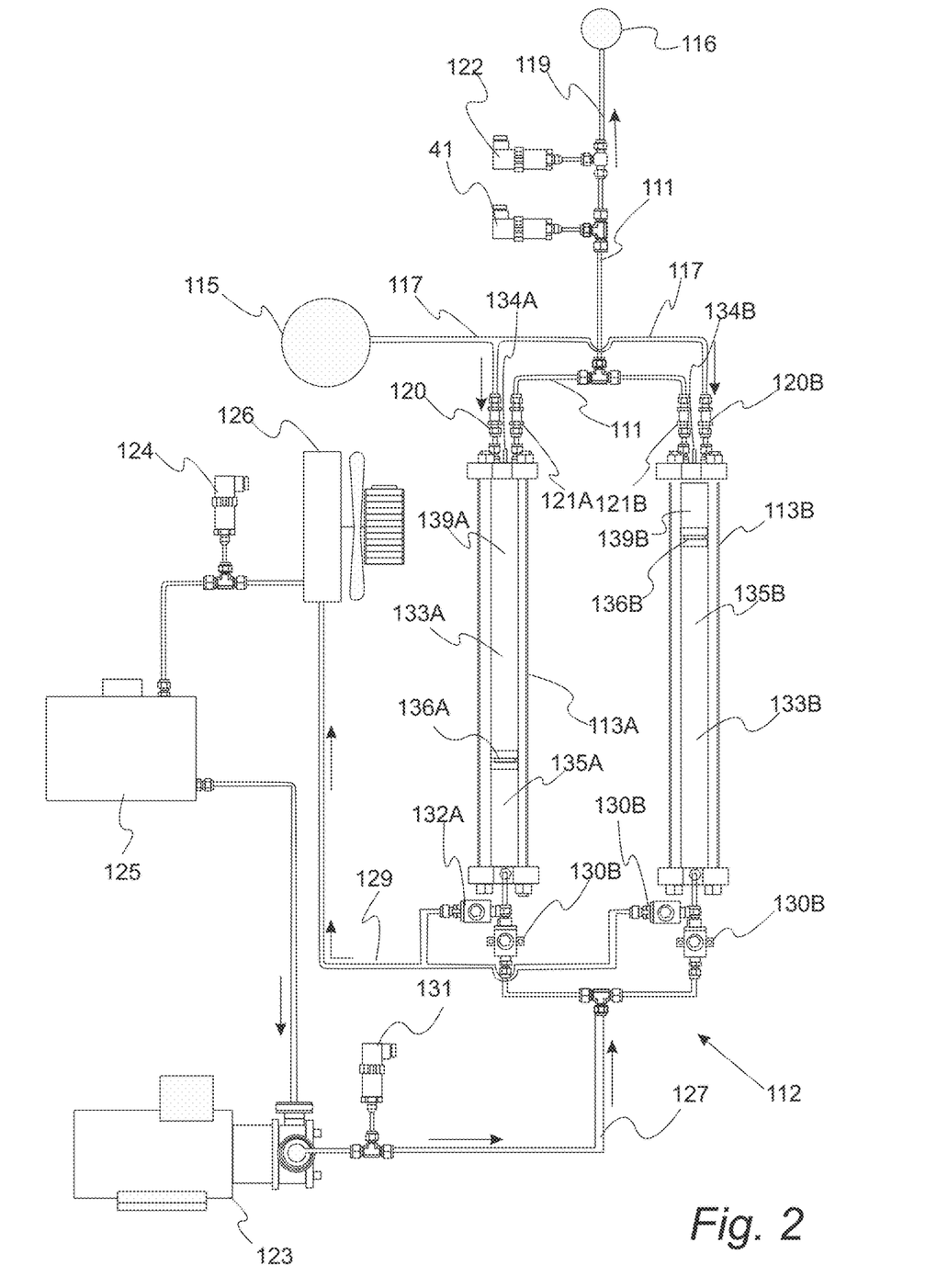
FIG. 2 illustrates a schematic illustration for a gas compression system with two independent compression organs.

FIG. 2 provides a schematic illustration for a gas compression system with two independent compression organs. The term "organ" as used herein mean device. Gas compression system 100, includes gas inlet tank 115. Gas inlet tank 115 is in fluid communication through inlet line 117 to the two compression organs 113A, 113B. The gas moves from inlet line 117 through inlet check valves 120A, 120B to the respective compression organs 113A, 113B. The gas flows from compression organs 113A, 113B through check valves 121A, 121B. A pressure sensor 122 operatively associated with outlet line 119 to detect the pressure of the compressed gas located inside outlet line 119. A temperature sensor 118 operatively associated with outlet line 119 detects the temperature of the compressed gas located inside outlet line 119. Downstream of the pressure sensor 122 and temperature sensor 118 is a gas outlet tank 116. The compressed gas moves from the two compression organs 113A, 113B via outlet line 119 to the gas outlet tank 116.

Each compression organ (113A, 113B) includes a hollow cylinders 133A, 133B, inside which a piston 136A, 136B is disposed transversely. The piston 136A is slidably positioned inside the cylinder 133A along a longitudinal direction so as to define two separate compartments (139A, 135A with variable volume inside each cylinder 133A. The piston 136B is slidably positioned inside the cylinder 133B along a longitudinal direction so as to define two separate compartments (139B, 135B with variable volume inside each cylinder 133B. The pistons 136A, 136B contact the inner circular surface of the cylinder 133A, 133B through respective sealing gaskets so the separate compartments are substantially isolated from one another.

The system of FIG. 2 also includes a control circuit 112 with a water pump 123, storage tank 125, radiator 126, intake line 127, and discharge line 129. The water pump 123 may be an electric pump or any suitable alternative. A control fluid circulates inside the control circuit 112. The control fluid in this instance is water. The intake line 127 connects the water pump 123 with the two compression organs 113A, 113B. The intake line 127 branches into two sections and transfers water to the two compression organs 113A, 113B by two respective exchange valves 130A, 130B. A pressure switch 131 is operatively associated with intake line 127 and located between water pump 123 and exchange valves 130A, 130B. Pressure switch 131 detects the pressure at which the water is pumped inside the intake line 127. The discharge line 129 is connected to the two compression organs 113A, 113B by corresponding exhaust valves 132A, 132B. A radiator 126 is located downstream of the exhaust valves 132A, 132B. A water temperature sensor 124 operatively associated with the discharge line 129 detects the temperature of the water in discharge line 129. The discharge line 129 connects the radiator 126 to a storage tank 125.

Inlet line 117 and outlet line 119 are in fluid connection with compartments 139A and 139B. Intake line 127 and discharge line 129 are in fluid connection with compartments 135A and 135B. In this way, compression circuit 111 and control circuit 112 are associated with opposite sides of each compression organ 113A, 113B.

The system exemplified in FIG. 2 operates as follows. Gas from gas inlet tank 115 is introduced through the inlet line 117 of the compression circuit 111. The gas moves through inlet line 117 and through inlet check valves 120A, 120B into compartment 139A of cylinder 133A and compartment 139B of cylinder 133B. The gas is introduced into compartments 139A and 139B at a pressure of approximately 4 bar. Sequentially or simultaneously with the flow of the gas, water is pumped from the storage tank 125 by the water pump 123. The water travels through intake line 27 of the control circuit 12 through exchange valves 130A into compartment 135A of cylinder 133A. The water pump 123 operates with a pressure such that it is sufficient to overcome the force caused by the gas during compression of the gas. This results in the piston 136A of cylinder 133A raising the piston 136A and compressing the gas located in compartment 139A. The compression causes the gas to exist from cylinders 133A through check valves 121A. The compressed gas from compartment 135A travels through outlet line 19 of the compression circuit 111 to gas outlet tank 116.

When the piston 136A in cylinder 133A reaches the limit switch, a magnetic sensor 134A detects a magnet present within piston 136. The magnet is isolated and is not in contact with any of the fluids present in the cylinder. The detection by magnetic sensor 134A activates exchange valve 130B and exhaust valve 132A and closes exchange valve 130A. Water present inside compartment 135A is evacuated due to the force of the gas which pushes the piston downwards. Water from compartment 135A is discharged and conveyed by discharge line 129 towards the radiator 126 where it is cooled to a predetermined temperature. The cooled water is temporarily stored in storage tank 125 before being pumped by water pump 123 back into intake line 127. The water is then directed towards cylinder 133B. Using similar methods as described with respect to cylinder 133A, the water pumped into compartment 135B of cylinder 133B compresses the gas introduced into compartment 139B. The compressed gas from compartment 135B travels through outlet line 119 of the compression circuit 111 to gas outlet tank 116.

The alternation of water pumping and gas compression exchange is repeated until pressure sensor 122 of the compression circuit 111 detects that the desired gas compression pressure has been reached inside gas outlet tank 116. The system of FIG. 2 may also operate with a single compression organ wherein the flow of water and gas into their respective compartments is sequential.

Figure 3:
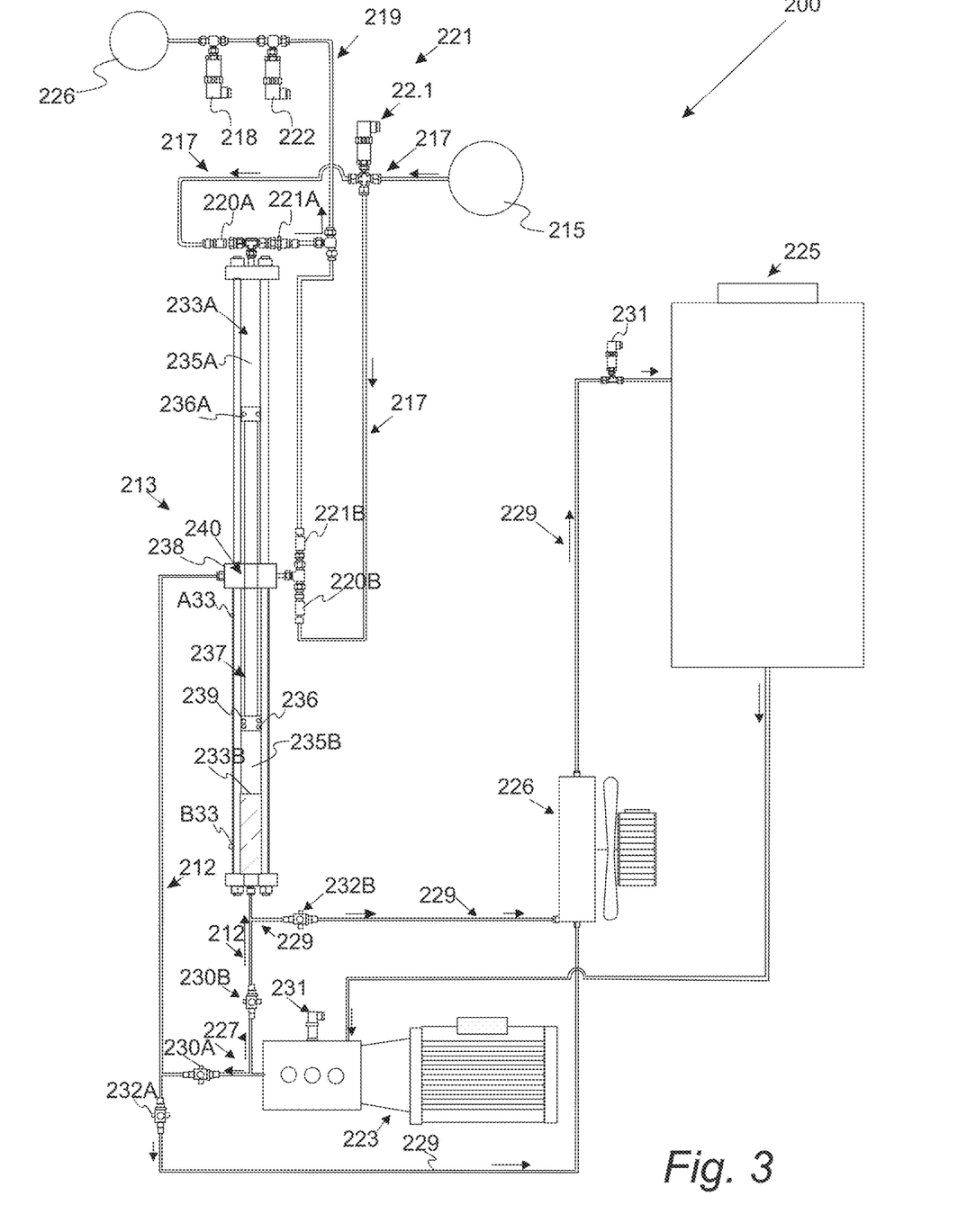
FIG. 3 illustrates another schematic illustration for a gas compression system with two overlapping compression organs.

FIG. 3 provides another schematic illustration for a gas compression system with two overlapping compression organs. In this example, gas compression system 200 includes a compression circuit 211, a control circuit 212, and a single compression organ 213 formed by two overlapping cylinders 233A, 233B. The compression circuit has a gas inlet tank 215 at one end and a gas outlet tank 216 at the other end. The gas inlet tank 215 is in fluid connection with inlet line 217. Inlet line 217 is in fluid connection with the compression organ via check valves 220A and 220B. A minimum pressure sensor 222.1 is operatively connected to inlet line 217 to prevent it from being pressure-free resulting in a vacuum. Check valves 221A, 221B are in fluid connection with the compression organ 213. An outlet line 219 is in fluid connection and downstream of check valves 221A, 221B. A pressure sensor 222 and a temperature sensor 218 are operatively associated and arranged to detect the pressure and temperature at which the compressed gas is located within the outlet line 219.

The compression organ 213 includes two hollow cylinders 233A, 233B inside which two pistons 236A, 236B are transversely connected by a stem 237. Both pistons 236A, 236B are slidable along a longitudinal direction and define compartments 235A, 235B. Piston 236A contacts the inner circular surface of cylinder 233A, while piston 236B contacts the inner circular surface of cylinder 233B. The cylinders 233A, 233B are separated by an intermediate flange 238 and sealing gasket 240 in which the stem 237 slides. Compartments 235C, 235D are formed between the sealing gasket and pistons 236A and 236B, respectively.

The system of FIG. 3 also includes a control circuit 212. The control circuit 212 includes a pump 223, an accumulation tank 225, a cooling radiator 226, a supply line 227 and a discharge line 229. The cooling radiator 226 may be an electro-ventilated cooler or any other reasonable substitute known to those skilled in the art. A control fluid circulates within the control circuit. The control fluid is preferably water. The pump 223 contains a pressure sensor 231 operatively associated and arranged to detect the pressure at which the fluid pumped inside the supply line 227.

The supply line 227 is in fluid connection with the pump 223 and the compression organ 213. The supply line 227 is divided into two branches by two exchange valves 230A, 230B, which are arranged between the pump 223 and cylinder 233B. The discharge line 229 is divided into two branches each connected to an outlet of the cylinder 233B by two related outlet valves 232A, 232B. The discharge line 229 also fluidly connects the cooling radiator 226 to the accumulation tank 225. The inlet line 217 and outlet line 219 of the compression circuit 211 are in fluid connection with compartment 235A of compression organ 213. Branches of the supply line 227 and discharge line 229 of the control circuit 212 are in fluid connection with 235B of compression organ 213.

The system exemplified in FIG. 3 operates as follows. Gas flows from gas inlet tank 215 through the inlet line 217 of the compression circuit 211 to compartment 235C of the cylinder 233A via check valve 220B. The gas is introduced at a pressure of approximately 2 bar. Simultaneously or sequentially, the pump 223 pumps fluid from accumulation tank 225 through supply line 227 of the control circuit towards the flange 238 into compartment 235D. Valves 230A, 232B are open. The pump 223 operates at a higher pressure on the fluid and is sufficient to overcome the force caused by the gas during the compression phase. This causes the pistons 236A, 236B to be lowered, compressing the gas in compartment 235C and causing it to exit through the check valve 221B. The compressed cases travel through the outlet line 219 of the compression circuit into the gas outlet tank 216.

When the piston 236B reaches the limit switch, the magnetic sensor B33 detects the magnet present in the piston 236B. The magnet is isolated and is not in contact with any of the fluids present in the cylinder 233B. Upon detection by the sensor B33, activation of the valves 230A and 232B occurs while at the same time the closing of valves 232A and 230B. The fluid is directed towards the cylinder 233A. The water inside compartment 235D is evacuated due to force of the water which pushes the piston upwards. The water drained travels by the discharge line 229 towards the cooling radiator 226 where its temperature is reduced. The cooled fluid is temporarily deposited in the accumulation tank 225 before being drawn by the pump 223 and re-pumped into the supply line 227.

The water is then pumped into compartment 235B of cylinder 233B. Gas flows through check valve 220A into compartment 235A of cylinder 233A. The pressure of the water flowing into compartment 235B causes the pistons 236A, 236B to be raised which compresses the gas in compartment 235A. The compressed gas exits the compartment 235A through valve 221A through the outlet line 219 of the compression circuit into the gas outlet tank 216.

Figure 4:
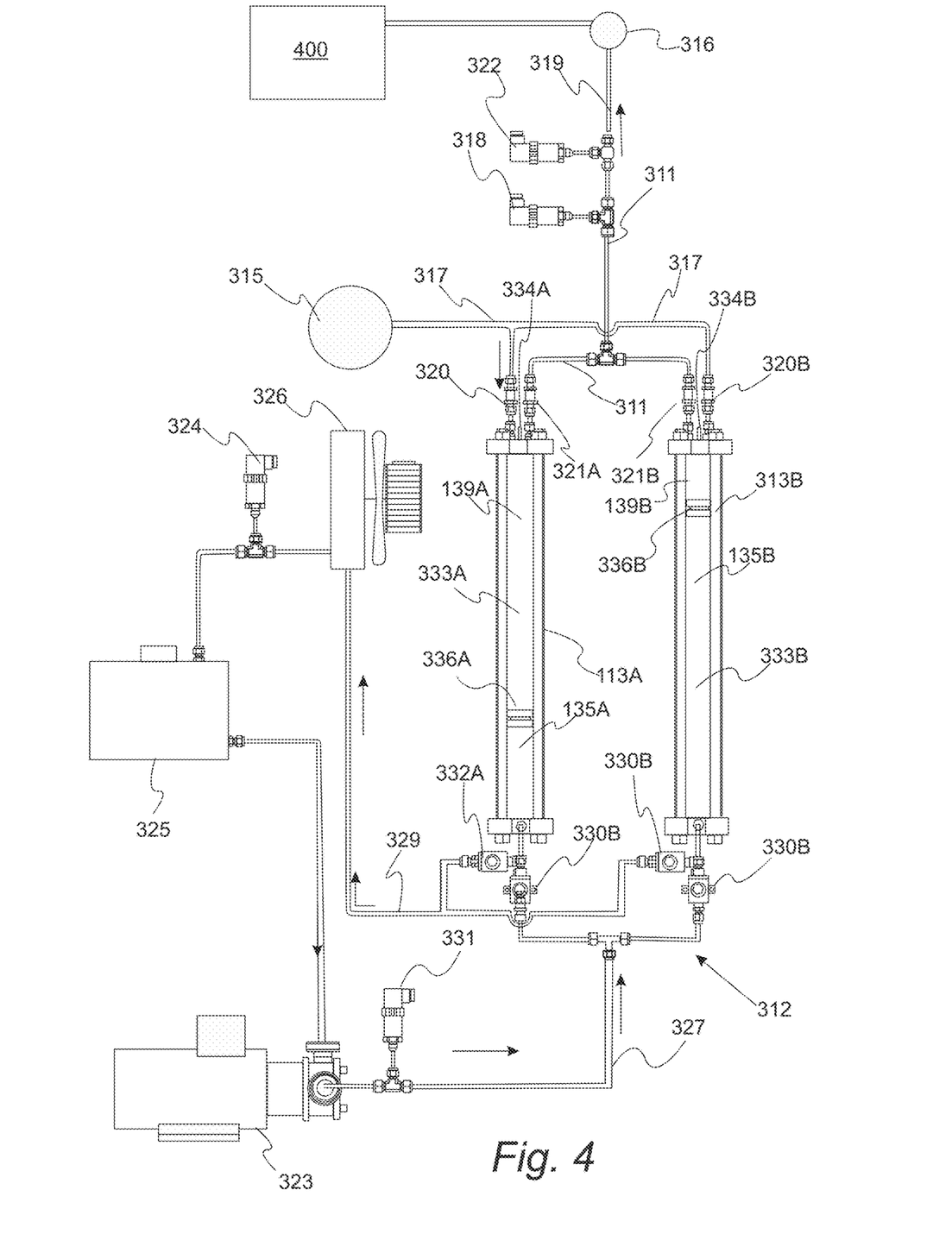
FIG. 4 illustrates another schematic illustration of a gas compression system coupled to a reactor.

Both the system of FIG. 2 and the system of FIG. 3 may be coupled to reactor as set forth in U.S. Pat. Nos. 7,910,787 and 10,099,199, the entirety of which are incorporated herein. The system of FIG. 4 illustrates the gas compression system of FIG. 2 coupled to a reactor system 400. Reactor system 400 facilitates gas-phase oxidation of a hydrocarbon-containing gas.

Figure 5:
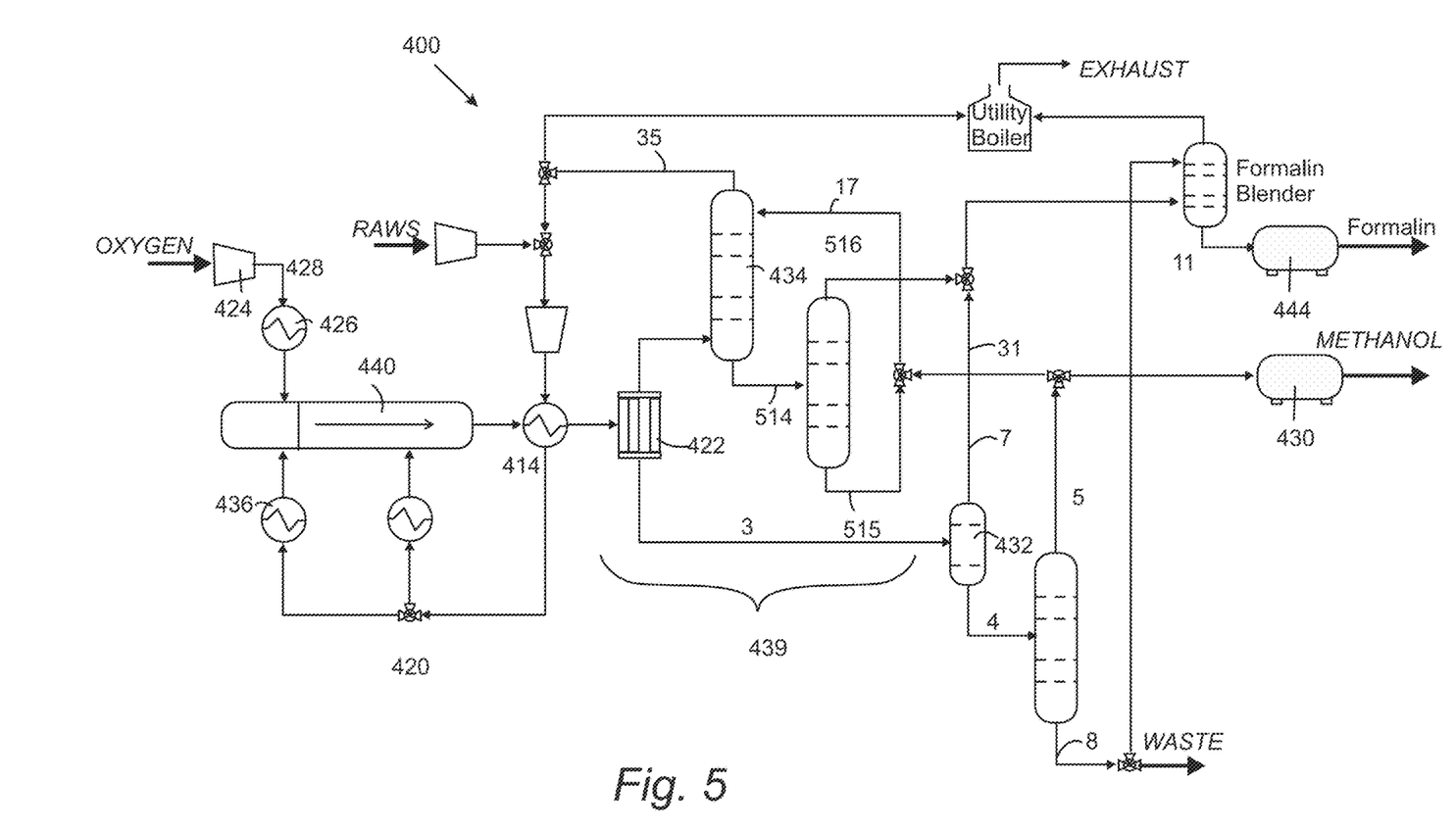
FIG. 5 illustrates another schematic showing a system of an apparatus for producing methanol coupled to a gas compression system.

FIG. 5 illustrates an exemplary schematic for the reactor system 400 coupled to a gas compression system 300. FIG. 5 details the inputs and outputs of the reactor. The reactor 440 has a reaction zone which is provided with a device for introducing a heated hydrocarbon-containing gas stream and a device for introducing an oxygen-containing compressed gas. The oxygen-containing compressed gas preferably has greater than 80% oxygen content to reduce the accumulation of inert gases by the recycling process.

The reactor 440 further has a regulation zone 408 provided with an optional device for introducing a cold hydrocarbon-containing gas stream for reducing the temperature of the reaction during operation of the apparatus. In addition, the reactor 440 is provided with thermal pockets for control and regulation of temperatures in corresponding zones, provided for example with thermocouples.

The apparatus has a device for cooling the reaction mixture before separation. Additionally, the partial condenser 422 incorporates a gas-liquid heat exchanger to further reduce the temperature of the products. The condenser 422 separates water and alcohols from a hydrocarbon-carbon dioxide mixture. The partial condenser 422 is preferably isobaric, as opposed to isothermal to avoid pressure losses. The product stream enters, and liquid stream and gaseous stream exist the condenser 422.

Block 439 represents equipment that is configured to separate contaminants and products from a hydrocarbon-containing recycle gas component. In this regard, block 439 is configured to remove carbon dioxide from the reduced product stream. The equipment 439 can take the form of a purge valve, absorber, membrane separator, or an absorber. It is envisioned the equipment 439 can be used to regulate the percentage of other non-reactive components such as nitrogen as with, for example, a purge valve.

In the event the system is configured to recover formaldehyde, the gaseous reduced product stream leaves the condenser 422 and is passed to the scrubber 434. Other potential methods that can be utilized use materials such as various amines known to remove $CO_2$ and formaldehyde. To fulfill the minimum absorption requirements, modification of the flow rate of methanol or operating temperature of the scrubber column can be used. If it is desirable to operate at extremely low absorbent flow rates, then a lower temperature can be utilized, for example 0° C. If it is desirable to operate at ambient temperatures or temperatures achievable via cooling water, then a high flow rate can be utilized, for example, ten times that of the flow rate for 0° C. In either scenario, the pregnant methanol absorbent stream 514 is completely regenerated by the formaldehyde distillation column 438. Optionally, the stream 514 from the scrubber 434 can be passed through the condenser 422 to provide cooling of the product stream and preheating of the methanol recycle to improve the energy efficiency of the formaldehyde distillation column 438.

The reactor 440 is connected with a compressor 424 and heater 426 for the supply of compressed and heated oxygen-containing gas. The raw hydrocarbon-containing gas is mixed with cleaned hydrocarbon gas from the scrubber 434 and is heated using a heater 436. In the event the raw hydrocarbons have a high $CO_2$ content, the raw hydrocarbons can be mixed with the reduced product hydrocarbon stream from the condenser 422 prior to the entry of the scrubber 434 for removal of contaminant gases prior to entering the reactor.

The apparatus further has a unit for rectification of methanol which includes a flash drum 432, rectification column 428, and a vessel 430 from which methanol is supplied to storage or further processing. This rectification column 428 is used to separate methanol (light-key component) from ethanol (heavy-key component) and water (non-key component). As before, it is desirable for a portion of the heavy key to enter the distillate stream (as dictated by commercial specification for formalin). For methanol rectification, 99% or higher purity is typical and 99.999% is achievable with multiple columns. Stream 4 enters the column and the distillate, stream 5, and bottoms, stream 8, exit the column in liquid phase. Stream 8 has some amount of ethanol (and perhaps methanol, if ultra-pure methanol was produced) and will be used as the basis of the aqueous makeup of the commercial formalin stream (stream 11). In this manner, some of the ethanol is recovered before the remainder is discarded in the liquid waste stream.

Disposed between the column 428 and the condenser 422 is a hash drum 432 for removal of $CO_2$ and formaldehyde from the liquid product stream. The purpose of the flash drum 432 is to drop the pressure to an appropriate level before entry into the methanol rectification column 428 and to substantially remove any dissolved gases, typically $CO_2$ and formaldehyde, from the liquid product stream.

In operation, the raw hydrocarbon-containing gas stream with a methane content for example up to 98% and the reduced hydrocarbon product stream are supplied from an installation for preparation of gas or any other source to the heater 436, in which it is heated to temperature 430-470° C. The heated hydrocarbon-containing gas is then supplied into the reaction zone of the reactor 440. Compressed air with pressure, for example, of 7-8 MPa and with a ratio 80% to 100% and, preferably, 90% to 95% oxygen is supplied by the compressor 424 also into the reaction zone of the reactor 440. Oxidation reaction takes place in the reaction zone of the reactor 440. Between 2% and 3% 0 2 of the total volume of the reactants are reacted with the heated hydrocarbon-containing gas stream as previously described. To limit the amount of $N_2$ within the system, for example to less than 30%-40%, or reduce the requisite size of the purge stream to achieve the same, the stream is preferably substantially pure, thus limiting the amount of $N_2$ entering the system.

An optional second stream of cold or in other words a lower temperature coolant than the gases in the reactor is supplied through the introducing device into the regulation zone of the reactor 440. This stream is regulated by the regulating device 420, which can be formed as a known gas supply regulating device, regulating valve or the like. This cold stream can be, for example, composed of a raw hydrocarbon stream, a recycled stream, or a portion or combination of the two. The regulator is configured to adjust the volume or pressure of cold hydrocarbon-containing gas based on system parameters such as, but not limited to, pressure, temperature or reaction product percentages downstream in the system.

The reaction mixture is supplied into the heat exchanger 414 for transfer of heat to the reactor input stream from the reaction mixture exiting the reactor, and after further cooling is supplied within partial condenser 422. Separation of the mixture into high and low volatility components, (dry gas and raw liquid, respectively) is performed in the partial condenser 422 which may absorb at least some of the formaldehyde into the raw liquid stream as desired. The dry gas is forwarded to a scrubber 434, while the raw liquids from the condenser 422 are supplied to the flash drum 432.

The scrubber 434 functions to remove the $CO_2$ and formaldehyde from the dry gas stream. In this regard, the scrubber 434 uses both $H_2O$ and methanol at between 7-8 MPa pressure and between about 0° C. and about 50° C. to absorb $CO_2$ and formaldehyde. Once the $CO_2$ and formaldehyde are removed, the reduced stream of hydrocarbon gas is recycled by mixing the reduced stream with the raw hydrocarbon-containing gas stream either before or within the reactor, as desired. The raw hydrocarbon and reduced streams, individually or in combination, are then inputted into the reaction chamber.

The rectification column is used to separate carbon dioxide (non-key component) and formaldehyde (light-key component) from methanol (heavy-key component) and water (non-key component). The pregnant methanol stream 514, enters the rectification column and is separated into a formaldehyde distillate, stream 516, and a bottoms stream, stream 515. Some amount of methanol in the distillate stream is desirable since methanol is used as a stabilizer for the production of commercial-grade formalin (6-15% alcohol stabilizer, 37% formaldehyde, and the balance being water). By allowing a portion of the heavy key into the distillate stream the separation is more easily achieved; furthermore, process losses typically experienced during absorbent regeneration are subsequently nullified as methanol within the distillate is used for formalin production. Stream 515 is supplemented by stream 31 so as to replace any methanol which was transferred to the distillate stream, stream 516. Combining stream 31 and stream 515 results in stream 17, which then returns to the scrubber 34 as regenerated methanol absorbent. Meanwhile, the formaldehyde distillate, stream 516, combines with the vapors from so flash drum 432, stream 7, to form a mixture of formaldehyde, methanol, and carbon dioxide.

The formaldehyde, water, methanol, and $CO_2$ removed by scrubber 434 are passed to formaldehyde rectification column 438. Column 438 removes formaldehyde and $CO_2$ from the methanol-water stream. Small amounts of methanol are combined with produced methanol and are inputted into the scrubber 434 to remove additional amounts of $CO_2$ and formaldehyde from the reduced hydrocarbon stream. Free or non-aqueous formaldehyde is allowed to remain in the gas phase by operation of the isobaric condenser 422. The liquid methanol product stream, or raw liquids, would then comprise methanol, ethanol, and water by allowing formaldehyde to remain in the gaseous stream. In this case, the liquid stream exiting the isobaric condenser 422 can bypass the formaldehyde rectification portion of the process and enter the methanol rectification column after having optionally passed through the flash drum 432.

Figure 6:
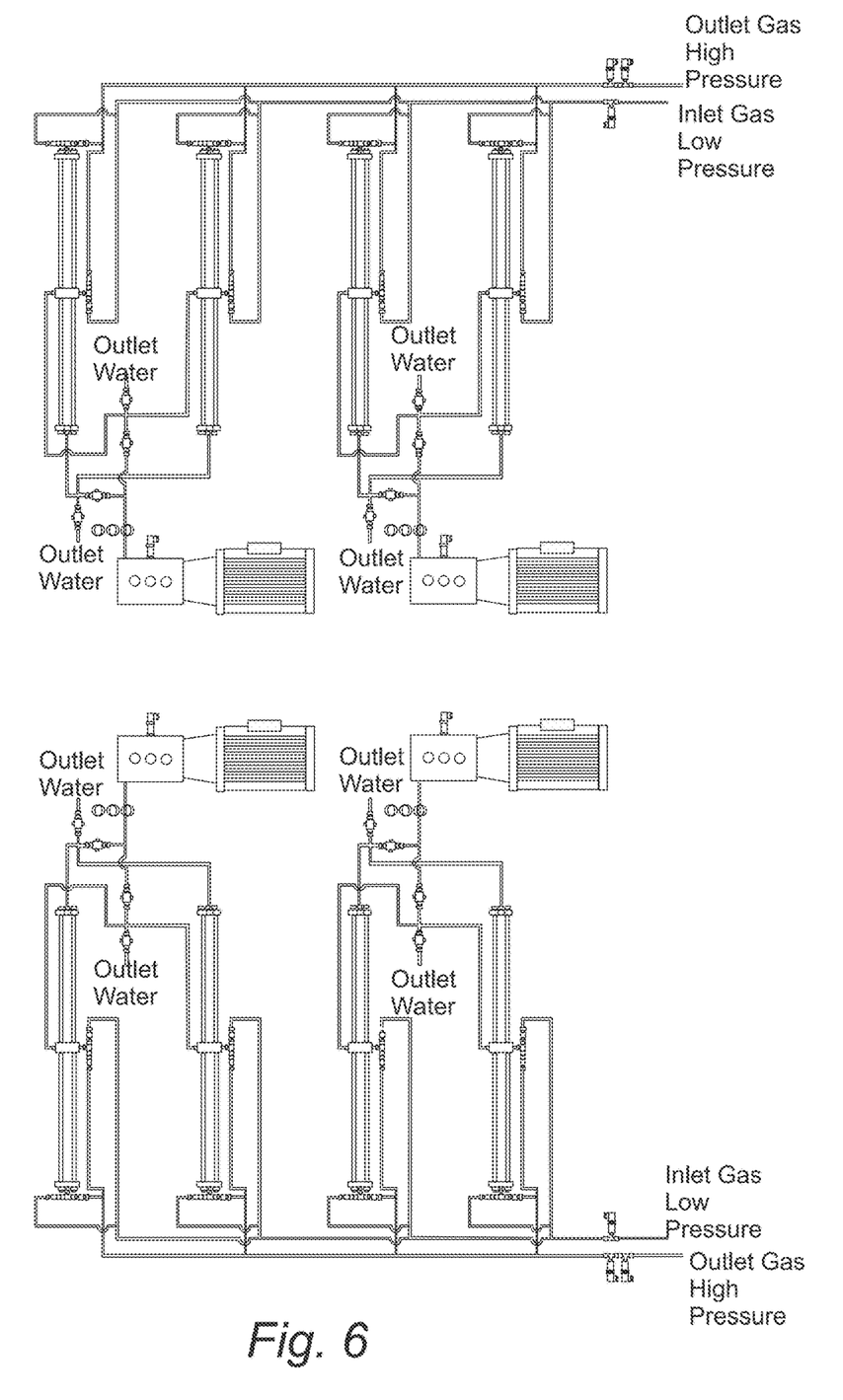
FIG. 6 illustrates another schematic showing a gas compression system.

FIG. 6 illustrates a schematic where the number of compression chambers is increased within a single system.

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

What is claimed is:

1. A gas compression system comprising:
a gas storage tank containing an uncompressed gas;
a liquid holding tank containing water;
a hollow cylinder in fluid connection with the gas storage tank and the liquid holding tank, the hollow cylinder having a bottom and a top;
a piston disposed within the hollow cylinder dividing the hollow cylinder into a first compartment and a second compartment;
a radiator in fluid connection with the second compartment of the hollow cylinder and the liquid holding tank, wherein the radiator cools water before it enters the liquid holding tank;
a gas collector tank in fluid connection with the first compartment of the hollow cylinder by an outlet line;
a pump in fluid connection with the liquid holding tank and second compartment of the hollow cylinder, wherein the pump moves water from the liquid holding tank into the second compartment; and wherein uncompressed gas enters the first compartment and the pump moves water into the second compartment at a higher pressure than the uncompressed gas causing the piston to move in a lateral direction resulting in a decrease in volume of the first compartment thereby compressing the uncompressed gas to a compressed gas;
a first valve positioned between the bottom of the hollow cylinder and the pump,
a second valve positioned between the bottom of the hollow cylinder;
a third valve positioned between the liquid holding tank and the second valve;
a magnet positioned at the top of the piston;

a first magnetic sensor positioned at the top of the hollow cylinder; and a second magnetic sensor positioned at the bottom of the hollow cylinder, wherein the first magnetic sensor and the second magnetic sensor detects the magnet present inside the piston such that detection of the magnet by the first magnetic sensor causes opening of second valve and third valve while closing the first valve such that the water is directed to liquid holding tanking by force of the compressed gas which pushes the piston in a downwards direction and wherein when the piston is detected by the second magnetic sensor, second valve and third valve close followed by the opening of the first valve thereby allowing the water to flow into the hollow cylinder to compress the uncompressed gas.

2. The gas compression system of claim 1 further comprising a temperature sensor operatively associated with the outlet line to measure temperature of a compressed gas.

3. The gas compression system of claim 1 further comprising a pressure sensor operatively associated with the outlet line to measure pressure of a compressed gas.

4. The gas compression system of claim 1 wherein a first check valve is disposed between the first compartment and the gas storage tank for entry of the uncompressed gas into the first compartment and a second check valve is disposed between the first compartment and the gas collector tank for exiting of compressed gas from the first compartment.

5. The gas compression system of claim 1 wherein a first exchange valve is disposed between the second compartment and the pump for entry of water into the second compartment and a second exchange valve is disposed between the second compartment and the radiator for exit of water following compression.

6. The gas compression system of claim 1 further comprising a limit switch operatively associated with the hollow cylinder.

7. The gas compression system of claim 1 further comprising:
- a second hollow cylinder in fluid connection with the gas storage tank and liquid holding tank; and
- a second piston disposed within the hollow cylinder dividing the hollow cylinder into a third compartment and a fourth compartment;
- wherein the third compartment is in fluid connection with the gas storage tank and gas collector tank;
- wherein the fourth compartment is in fluid connection with the pump and the radiator; and
- wherein uncompressed gas enters the third compartment and the pump moves water into the fourth compartment at a higher pressure than the uncompressed gas causing the piston to move in a lateral direction resulting in a decrease in volume of the third compartment thereby compressing the uncompressed gas.

8. A gas compression system comprising:
- a first cylinder having a bottom and a top;
- a second cylinder connected to the first cylinder by a sealing gasket;
- a piston assembly comprising:
  - a first piston disposed in the first cylinder defining a first compartment between the first piston and the sealing gasket;
  - a second piston disposed in the second cylinder defining a second compartment between the second piston and the sealing gasket; and
  - a stem connecting the first piston and the second piston;
- a gas storage tank in fluid connection with the first cylinder and first compartment;
- a liquid holding tank in fluid connection with the second compartment and second cylinder, the liquid holding tank containing water;
- a pump in fluid connection with the liquid holding tank;
- a gas collector tank in fluid connection with the second compartment and first cylinder by an outlet line; and
- a radiator in fluid connection with the second cylinder, second compartment, and liquid holding tank;
- a first valve positioned between the bottom of the first cylinder and the pump,
- a second valve positioned between the bottom of the first cylinder;
- a third valve positioned between the liquid holding tank and the second valve;
- a magnet positioned at the top of the first piston;
- a first magnetic sensor positioned at the top of the first cylinder; and
- a second magnetic sensor positioned at the bottom of the first cylinder,
- wherein uncompressed gas enters the first compartment and water enters the second compartment at a higher pressure than the uncompressed gas resulting in lateral movement of the piston assembly thereby compressing the uncompressed gas to compressed gas;
- wherein uncompressed gas enters the first cylinder and water enters the second cylinder at a higher pressure than the uncompressed gas resulting in lateral movement of the piston assembly thereby compressing the uncompressed gas to compressed gas; and
- wherein the first magnetic sensor and the second magnetic sensor detects the magnet present inside the first piston such that detection of the magnet by the first magnetic sensor causes opening of second valve and third valve while closing the first valve such that the water is directed to liquid holding tanking by force of the compressed gas which pushes the first piston in a downwards direction and wherein when the first piston is detected by the second magnetic sensor, second valve and third valve close followed by the opening of the first valve thereby allowing the water to flow into the first cylinder to compress the uncompressed gas.

9. The gas compression system of claim 8 further comprising a temperature sensor operatively associated with the outlet line to measure a temperature of compressed gas.

10. The gas compression system of claim 8 further comprising a pressure sensor operatively associated with the outlet line to measure a pressure of compressed gas.

11. The gas compression system of claim 8 wherein a first check valve is disposed between the gas storage tank and the first cylinder, a second check valve is disposed between the first cylinder and the gas collector tank, a third check valve is disposed between the gas storage tank and the first compartment, and a fourth check valve is disposed between the first compartment and the gas storage tank.

12. The gas compression system of claim 8 wherein a first exchange valve is disposed between the second cylinder and the pump, a second exchange valve is disposed between the second cylinder and the radiator, a third exchange valve is disposed between the second compartment and the pump, and a fourth exchange valve is disposed between the second compartment and the radiator.

13. The gas compression system of claim 8 further comprising a first limit switch and a second limit switch lateral spaced and operatively associated with the second cylinder.

14. The gas compression system of claim 13 wherein the second piston contains a magnet that interacts with the first limit switch and second limit switch to open and close exchange valves.

15. A reaction assembly comprising:
- a reactor system that oxidizes a hydrocarbon-containing gas; and a gas compression system that includes gas compression system comprising:
- a gas storage tank containing an uncompressed gas;
- a liquid holding tank containing water;
- a hollow cylinder in fluid connection with the gas storage tank and the liquid holding tank, the hollow cylinder having a bottom and a top;
- a piston disposed within the hollow cylinder dividing the hollow cylinder into a first compartment and a second compartment;
- a radiator in fluid connection with the second compartment of the hollow cylinder and the liquid holding tank, wherein the radiator cools water before it enters the liquid holding tank;
- a gas collector tank in fluid connection with the first compartment of the hollow cylinder by an outlet line;
- a pump in fluid connection with the liquid holding tank and second compartment of the hollow cylinder, wherein the pump moves water from the liquid holding tank into the second compartment; and wherein uncompressed gas enters the first compartment and the pump moves water into the second compartment at a higher pressure than the uncompressed gas causing the piston to move in a lateral direction resulting in a decrease in volume of the first compartment thereby compressing the uncompressed gas to a compressed gas;
- a first valve positioned between the bottom of the hollow cylinder and the pump,
- a second valve positioned between the bottom of the hollow cylinder;
- a third valve positioned between the liquid holding tank and the second valve;
- a magnet positioned at the top of the piston;
- a first magnetic sensor positioned at the top of the hollow cylinder; and
- a second magnetic sensor positioned at the bottom of the hollow cylinder, wherein the first magnetic sensor and the second magnetic sensor detects the magnet present inside the piston such that detection of the magnet by the first magnetic sensor causes opening of second valve and third valve while closing the first valve such that the water is directed to liquid holding tanking by force of the compressed gas which pushes the piston in a downwards direction and wherein when the piston is detected by the second magnetic sensor, second valve and third valve close followed by the opening of the first valve thereby allowing the water to flow into the hollow cylinder to compress the uncompressed gas.

16. The reaction assembly of claim 15 comprising a temperature sensor operatively associated with the outlet line to measure a temperature of compressed gas.

17. The reaction assembly of claim 15 further comprising a pressure sensor operatively associated with the outlet line to measure a pressure of compressed gas.

18. The reaction assembly of claim 15 wherein a first check valve is disposed between the first compartment and the gas storage tank for entry of the uncompressed gas into the first compartment and a second check valve is disposed between the first compartment and the gas collector tank for exit of compressed gas from the first compartment.

19. The reaction assembly of claim 15 wherein a first exchange valve is disposed between the second compartment and the pump for entry of water into the second compartment and a second exchange valve is disposed between the second compartment and the radiator for exit of water following compression.

20. The reaction assembly of claim 15 further comprising a limit switch operatively associated with the hollow cylinder.

21. The reaction assembly of claim 20 wherein the piston contains a magnet that interacts with the limit switch to open and close exchange valves.

* * * * *